(12) United States Patent
Horne et al.

(10) Patent No.: US 6,211,361 B1
(45) Date of Patent: Apr. 3, 2001

(54) METHOD FOR MAKING DEBROMOHYMENIALDISINE AND ANALOGS THEREOF

(75) Inventors: David A. Horne; Kenichi Yakushijin, both of Corvallis, OR (US)

(73) Assignee: State of Oregon acting by and through The Oregon State Board of Higher Education on behalf of Oregon, State Univeristy, Corvallis, OR (US)

( * ) Notice: Subject to any disclaimer, the term of this patent is extended or adjusted under 35 U.S.C. 154(b) by 0 days.

(21) Appl. No.: 09/357,687

(22) Filed: Jul. 20, 1999

(51) Int. Cl.[7] .................................................. C07D 487/04

(52) U.S. Cl. ............................................................ 540/521

(58) Field of Search ............................................. 540/521

(56) References Cited

U.S. PATENT DOCUMENTS

| | | | |
|---|---|---|---|
| 5,565,448 | * 10/1996 | Nambi et al. | 514/215 |
| 5,591,740 | * 1/1997 | Chipman et al. | 514/215 |
| 5,621,099 | * 4/1997 | Annoura et al. | 540/521 |

* cited by examiner

*Primary Examiner*—Bruck Kifle
(74) *Attorney, Agent, or Firm*—Klarquist Sparkman Campbell Leigh & Whinston, LLP

(57) ABSTRACT

A method for making debromohymenialdisine (DBH) 2 and analogs thereof is described. One embodiment of the present method first comprises forming hymenin 4, and then converting hymenin into DBH 2 as described herein. One such embodiment first comprises providing a compound having Formula 3

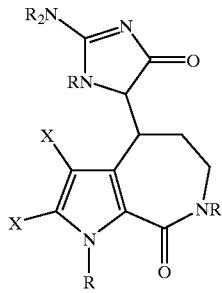

Formula 3 where R is independently selected from the group consisting of hydrogen and lower aliphatic, and X is independently selected from the group consisting of hydrogen and halogen. A compound having Formula 3, such as Compound 10 with R and X as hydrogen, is then converted to DBH 2 or an analog thereof. An alternative embodiment of the method comprises forming Compound 30 or Compound 32, which are then directly converted to DBH 2. Alternatively, Compound 30 can be converted to Compound 10, which is then subsequently converted to DBH 2 by reaction with a halogen in the presence of an acid. The method of the present invention can be used to make analogs of DBH 2, including alkoxy derivatives, such as Compound 12, and conjugated diene derivatives, such as Compound 14.

78 Claims, No Drawings

METHOD FOR MAKING DEBROMOHYMENIALDISINE AND ANALOGS THEREOF

ACKNOWLEDGEMENT OF GOVERNMENTAL SUPPORT

The present invention was developed, at least in part, using governmental funds provided by the National Institutes of Health under contract number GM 50929-05. The United States government may have rights to this invention.

FIELD

The present invention concerns a method for making debromohymenialdisine and analogs thereof, and analogs made by the method.

BACKGROUND

Debromohymenialdisine (DBH) 2 is a $C_{11}N_5$ marine sponge alkaloid that was first isolated from an Okinawan sponge, Hymeniacidon sp.

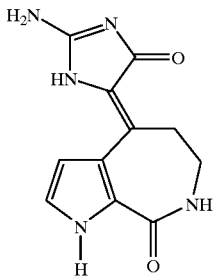

Compound 2

Horne et al., "Synthesis of $C_{11}N_5$ Marine Sponge Alkaloids: (±)-Hymenin, Stevensine, Hymenialdisine, and Debromohymenialdisine," *J. Org. Chem.*, 62:456–464, 456 (1997).

Known analogs of DBH include hymenin 4, stevensine 6, and hymenialdisine 8.

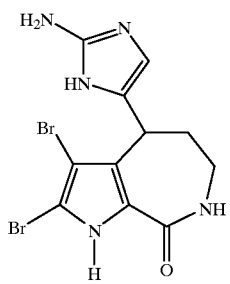

Compound 4

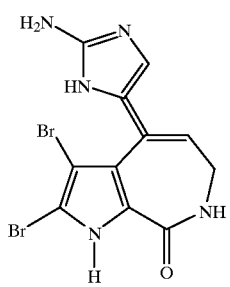

Compound 6

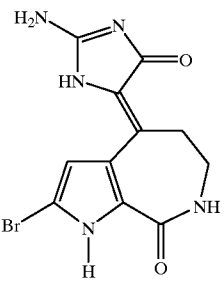

Compound 8

These natural products are the primary family members of the sponge metabolites that contain a fused pyrrolo[2,3-c]azepin-8-one ring system having either a 2-aminoimidazole or glycocyamidine appendage. Id.

Hymenin 4 has been shown to have potent α-adrenoreceptor-blocking properties. Kobayashi, J. et al., *Experientia* 42; 1064 (1986); Kobayashi, J. et al. *The Alkaloids: Chemistry and Pharmacology*, 41: 41–124 (1992); and Faulkner, D. J., *J. Nat. Prod. Rep.*, 13: 75 (1996). Moreover, DBH 2 can be used to treat subjects having osteooarthritis, which is a progressive, irreversible disease characterized by pain and loss of function caused by cartilage degradation. Chipman et al., U.S. Pat. No. 5,591,740 (the '740 patent), column 1, lines 7–18. Osteoarthritis can result in the complete erosion of weight-bearing articular cartilage, which may require total joint replacement. Id. Pro-inflammatory cytokine interluekin-1 (IL1) apparently plays a role in the cartilage matrix destructive processes observed in osteoarthritis. Pelletier et al., *Sem. Arth. Rheum.*, 20:12 (1991); and McDonnell, et al., *Arth. Rheum.*, 35:799 (1992).

Prior to the Chipman et al. invention described in the '740 patent, there were few, if any, therapeutic approaches that effectively slowed the clinical progression of osteoarthritis. The '740 patent, supra. The method for treating subjects having osteoarthritis described in the '740 patent comprises administering to individuals therapeutically effective amounts of DBH.

A commercially viable and efficient method for making DBH, and biologically active analogs thereof, is required to treat the number of patients having osteoarthritis, and other afflictions, who potentially might benefit from such treatments. Some methods are known for making hymenialdisine and DBH. See, for example, Horne et al., *J. Org. Chem.* 51:456–464 (1997), supra; Horne et al., U.S. Pat. No. 5,834,609, incorporated herein by reference; Horne et al., U.S. patent application Ser. No. 09/016,748, which is incorporated herein by reference; and Annoura et al., U.S. Pat. No. 5,621,099. These prior syntheses do not provide commercially viable methods for making DBH for several reasons, including (1) the yield of DBH is too low in the final step or steps of the synthesis, (2) the prior methods require too many synthetic steps overall, and (3) purification of the products. Therefore, despite these previous approaches, a more efficient and economically viable method for synthesizing bicyclic aminoimidazoles, such as DBH and analogs thereof, is needed.

SUMMARY

The present invention provides a method for making DBH and analogs thereof that addresses the problems associated with prior methods, such as by decreasing the number of steps of the synthesis and/or by increasing the overall yield of DBH or analogs thereof. The method of the present invention comprises providing hymenin 4, and then converting hymenin 4 into debromohymenialdisine 2, and analogs thereof, in the manner described herein.

As used herein, "analog" generally refers to compounds satisfying formulas stated in this application where R groups are hydrogen or aliphatic groups, particularly lower (10 carbon atoms or less) alkyl groups, X groups are hydrogen or halogen, particularly bromine, and combinations thereof. "Analog" also can refer to compounds having different ring structures, such as those exemplified by hymenin 4, stevensine 6, hymenialdisine 8, and the formulas provided herein.

Unless stated otherwise, variable groups on formulas provided in this application are as follows: $C_1$ and $C_2$ are carbon atoms bonded together by a single bond or a double bond; R is independently selected from the group consisting of hydrogen and lower aliphatic groups, particularly lower alkyl; R' is selected from the group consisting of hydrogen, lower aliphatic, particularly lower alkyl, and alkoxy, particularly lower alkoxy; and X is independently selected from the group consisting of hydrogen and halogen.

One embodiment of the present method for converting hymenin 4 to debromohymenialdisine 2 and analogs thereof comprises first forming a compound having Formula 1 or Formula 2 below. With reference to Formula 1,

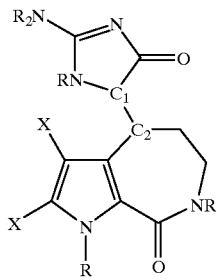

Formula 1

X is hydrogen when $C_1$ and $C_2$ are carbon atoms in a single bond and is a halogen when $C_1$ and $C_2$ are carbon atoms in a double bond. With reference to Formula 2,

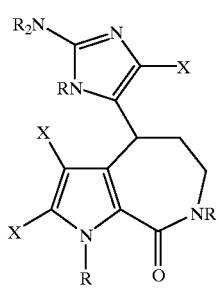

Formula 2

X is independently selected from the group consisting of hydrogen and halogen other than bromine. If $C_1$ and $C_2$ are carbon atoms in a single bond, converting hymenin to debromohymenialdisine can comprise first providing a compound having Formula 3

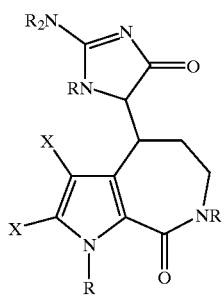

Formula 3 where X is independently selected from the group consisting of hydrogen and halogen when any one of R is lower alkyl and is hydrogen when R is hydrogen. One example of a compound having Formula 3 is Compound 10

Compound 10

Compound 10 can be converted to debromohymenialdisine 2 by reaction with a halogen, such as bromine, typically in the presence of an acid, such as methane sulfonic acid. Converting Compound 10 to debromohymenialdisine 2 in this manner provides a distinct advantage over prior syntheses in that such approach is substantially more efficient than prior syntheses.

The method of the present invention also can comprise providing a compound having Formula 4

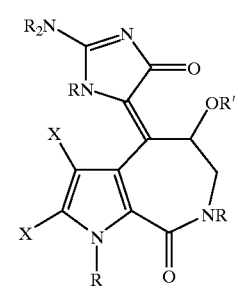

Formula 4 and then converting such compounds to compounds having Formula 3. One example of a compound having Formula 4 is Compound 12

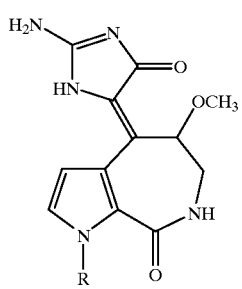

Compound 12

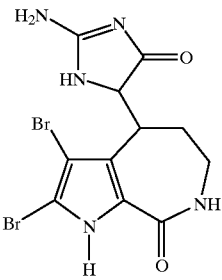

Compound 28

Compounds having Formula 4 typically are converted to compounds having Formula 5

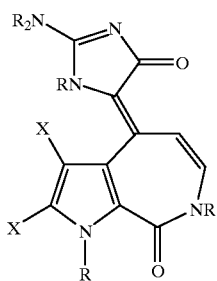

Formula 5

In such cases, the method can comprise providing a compound where all R and X groups are hydrogen in Formula 5, and converting comprises first forming the compound having Formula 3 with all R and X hydrogen by reaction with, for example, hydrogen and a catalyst, and then forming debromohymenialdisine 2.

Providing a compound having Formula 3 can be accomplished by first providing a compound having Formula 2 where X is halogen, and then converting the compound having Formula 2 to a compound having Formula 3 where R and X are hydrogen. One example of a compound having Formula 2 where R is hydrogen and X is bromine is Compound 26

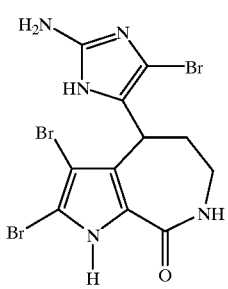

Compound 26

Compound 26 can be converted to a compound having Formula 3 by heating the compound in an acidic aqueous solution, such as an acetic acid solution.

Converting a compound having Formula 2 to a compound having Formula 3 also can comprise forming Compound 28 and then reacting such compound with hydrogen and a catalyst. The present invention also can comprises converting hymenin directly, i.e., without any intermediate steps, to a compound having Formula 3, such as Compound 28. This provides a substantial advantage with respect to known syntheses, which require forming additional intermediates between hymenin and Compound 28.

$C_1$ and $C_2$ of Formula 1 also can be connected by a double bond, such as with Compound 30

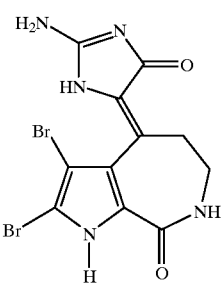

Compound 30

Compound 30, and analogs thereof, can be directly converted to debromohymenialdisine 2 using hydrogen and a catalyst, including metal-based catalysts, particularly palladium-based catalysts and platinum-based catalysts, Lindlar's catalyst and Raney nickel. Such compounds also can be converted to debromohymenialdisine 2 using a metal and a mineral acid, such as zinc and hydrochloric acid. Alternatively, Compound 30 can be converted to Compound 10, which is then subsequently converted to debromohymenialdisine 2 by reaction with a halogen in the presence of an acid.

Still another embodiment of the method of the present invention comprises forming a compound having Formula 2 with X being hydrogen. Such compounds are then oxidized to debromohymenialdisine 2, or an analog thereof, such as by using copper acetate, aqueous sodium hydroxide or palladium and hydrogen. This route provides an advantage relative to known syntheses by substantially reducing the number of steps required to form the final product.

Still another embodiment of the present invention comprises forming hymenin directly from compounds having Formula 6

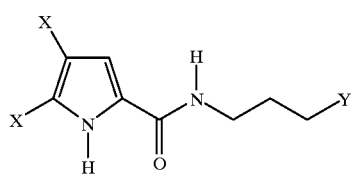

Formula 6 without isolating an intermediate where X is a halogen and Y is a selected from the group consisting of an aldehyde, a functional group capable of conversion to an aldehyde, such as a carboxylic acid group, and a protected aldehyde.

Several embodiments of the present invention comprise providing compound 10

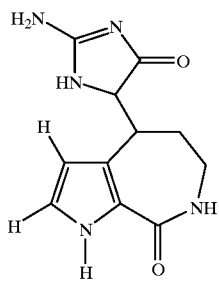

Compound 10 and then converting Compound 10 to debromohymenialdisine 2. Providing Compound 10 can comprise converting hymenin 4 directly to Compound 26

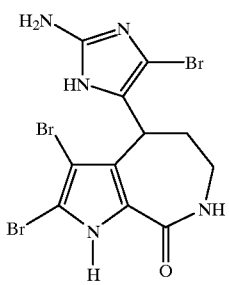

Compound 26 converting Compound 26 to Compound 28

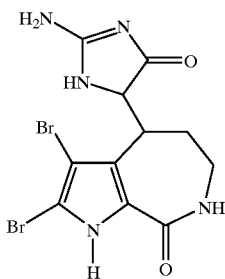

Compound 28 and converting compound 28 to compound 10. Alternatively, the method can comprise converting hymenin 4 directly to compound 28, and converting compound 28 to compound 10.

Still another embodiment of the present invention comprises converting hymenin directly to Compound 32

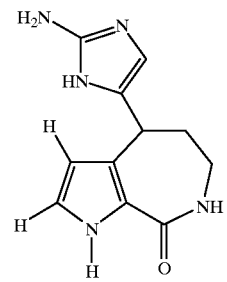

Compound 32 and then converting Compound 32 to debromohymenialdisine 2. This can be done directly by reacting such compound with copper acetate, aqueous sodium hydroxide or palladium and oxygen.

The present invention also provides compounds having Formula 7

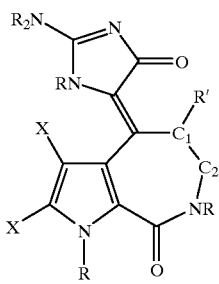

Formula 7

With reference to Formula 7, R' is hydrogen when $C_1$ and $C_2$ are bonded together by a double bond and is selected from the group consisting of hydrogen and lower alkoxy when $C_1$ and $C_2$ are bonded together by a single bond. Examples of compounds having this formula included compounds where $C_1$ and $C_2$ are bonded together by a single bond, where R' is lower alkoxy, where all R groups are hydrogen, where all X groups are hydrogen, where all R groups are hydrogen and R' is lower alkoxy, and where all R groups are hydrogen, R' is lower alkoxy and all X groups are halogen. A particular example of such compounds includes Compound 12

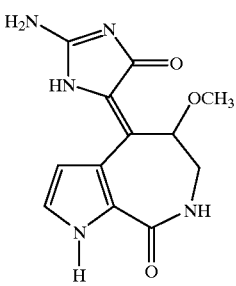

Compound 12

Compounds of the present invention also can have $C_1$ and $C_2$ bonded together by a double bond. An example of such a compound is Compound 14

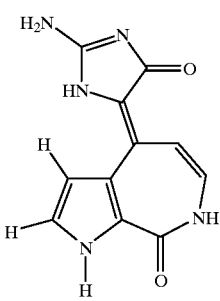

Compound 14

DETAILED DESCRIPTION

I. Method for Making DBH and Analogs Thereof

The present invention provides a method for making debromohymenialdisine (DBH) 2 comprising first forming hymenin 4, or an analog thereof, and then converting this compound into DBH 2, or analogs thereof. For example, hymenin 4 can be converted into compounds having Formula 3, which are then converted into DBH 2 and analogs and homologs of DBH.

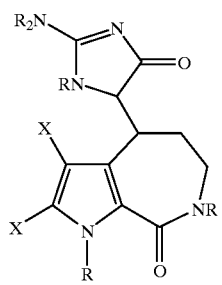

Formula 3

With reference to Formula 3, R is independently selected from the group consisting of hydrogen and lower aliphatic, particularly lower alkyl, and X is selected from the group consisting of hydrogen and halogen, particularly bromine. As used herein, "lower" refers to compounds having 10 or fewer carbon atoms in a chain, and includes all branched chain isomers and stereoisomers of such compounds. A currently preferred method for making DBH 2 proceeds by first making compound 10, and then converting compound 10 into DBH. These embodiments of the present method are illustrated in Schemes 1–3.

DBH 2 and analogs thereof also can be made by first making compounds having Formula 1 where $C_1$ and $C_2$ are bonded together by a single bond, R is hydrogen, and X is halogen. Such compounds then can be converted directly into DBH 2, and analogs thereof. Alternatively, such compounds can be converted into compound 10, such as by catalytic hydrogenation, and then converted into DBH 2 and analogs thereof. These embodiments of the present invention are illustrated in Scheme 3.

Scheme 4 illustrates another alternative embodiment of the present invention whereby hymenin 4 is first formed, and then compounds having general Formula 2 are formed by reducing hymenin 4. Compound 32 and analogs thereof are then converted to DBH 2 and analogs thereof by an oxidation reaction.

A. Scheme 1

Scheme 1 illustrates a working embodiment for making compound 10. Scheme 1 also provides one working embodiment of a method for converting compound 10 into DBH 2.

Scheme 1

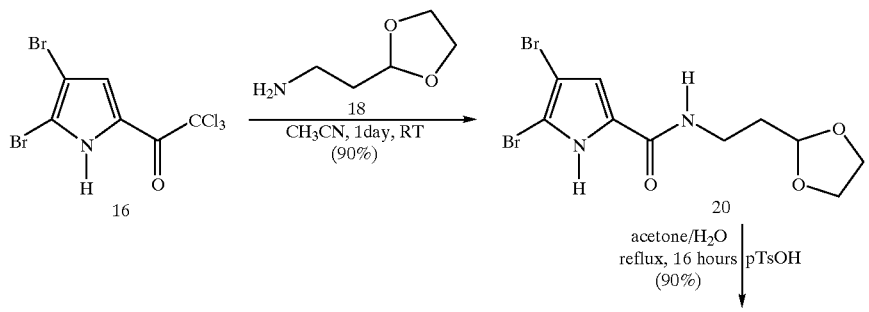

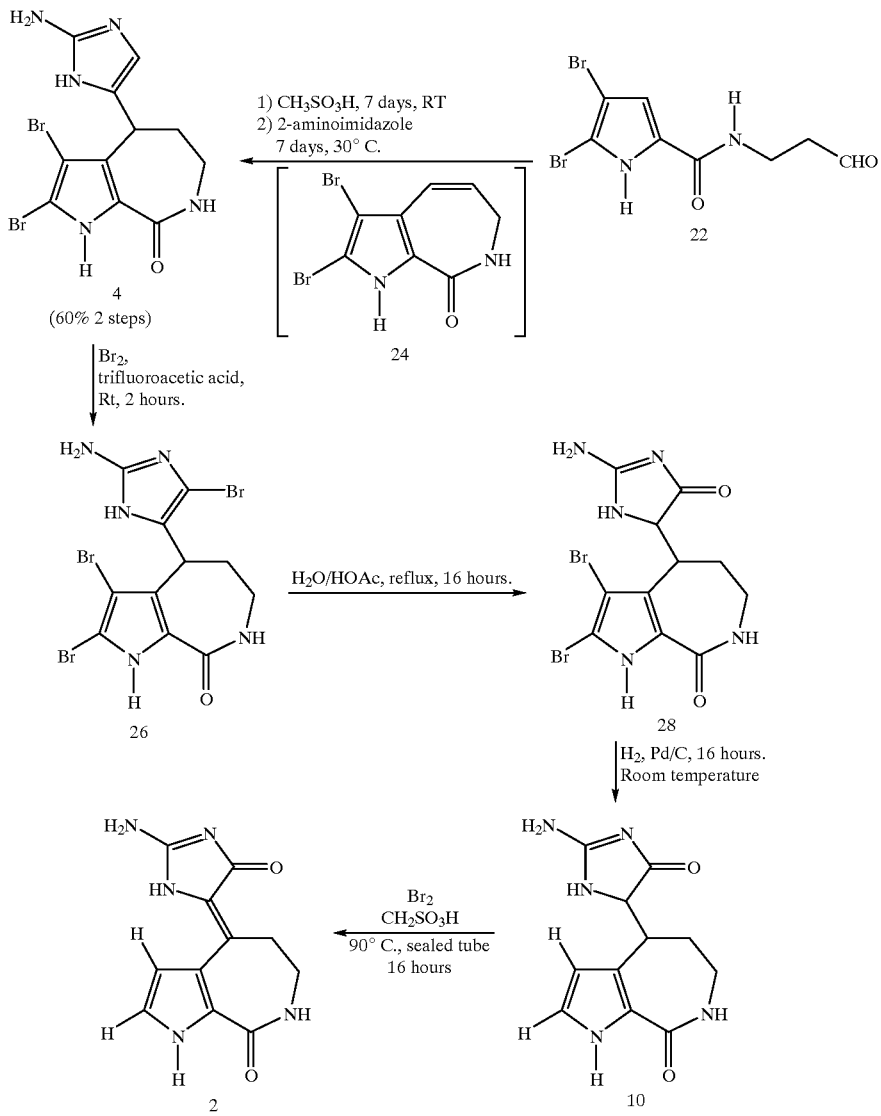

Details concerning the synthesis of compounds of Scheme 1 (except compound 10 and the method for converting compound 10 to DBH 2) are provided in applicants' issued U.S. Pat. No. 5,834,609, which is incorporated herein by reference, and in the examples. Example 7 provides details for a working embodiment of a method for making compound 10, and Example 8 provides details for a working embodiment of a method for converting compound 10 into DBH 2.

With reference to Scheme 1, the first step illustrated is the coupling of bromopyrrole 16 with amine 18. Amine 18 includes an acetal, which can be hydrolyzed to provide aldehyde 22. A person of ordinary skill in the art will realize that the acetal functions as an aldehyde protecting group. Other suitable protecting groups also could be used, such as those described in Theodora Greene's *Protecting Groups in Organic Syntheses,* (Wiley Science, 1984), and later editions, all of which are incorporated herein by reference. Furthermore, the first reaction shown is the formation of an amide. Other methods for forming amides are known in the art, and such reactions likely can be used to form amide 20.

The second reaction illustrated in Scheme 1 is the formation of aldehyde 22 by acetal hydrolysis. Other conditions for hydrolyzing the acetal also likely will work. Moreover, if a different protecting group is provided, then the conditions for forming aldehyde 22 would be those conditions most suitable for removing such protecting group.

Scheme 1 illustrates the formation of hymenin 4 by intramolecular cyclization of aldehyde 22 through intermediate 24. Methane sulfonic acid was selected as a suitable solvent for performing this reaction because it provides: (1) a proton source; and (2) a sufficiently high boiling point to provide sufficient heating of the reaction mixture to allow for efficient intramolecular cyclization. Other solvents also would work for this reaction, as long as such solvents satisfy the two criteria stated above. Once the intramolecular cyclization to form Compound 24 is complete, 2-aminoimidazole is then coupled to Compound 24, which need not be isolated, to provide hymenin 4.

Hymenin 4 is then halogenated. Because some of the DBH analogs are brominated, the halogen of choice for this reaction is bromine. However, DBH 2 does not include a halogen, and hence other halogens, such as chlorine, could be used to halogenate hymenin 4 to produce halogenated analogs of the illustrated compound 26. The halogenated compound 26 is then reacted with water and an acid, such as acetic acid, to form dehalogenated compound 28.

Compound 28 is hydrogenated to remove bromine atoms and form compound 10, which is then oxidized in the presence of bromine and methane sulfonic acid to form DBH 2. Other oxidizing conditions also may be used to form DBH 2. For example, palladium on carbon, lead tetraacetate, DDQ, ceric ammonium nitrate, mercuric acetate, and electrochemical oxidation, also can be used to oxidize compound 10 to form DBH 2.

B. Scheme 2

Scheme 2 illustrates an alternative method for synthesizing DBH 2, which involves fewer synthetic steps than Scheme 1. Those synthetic procedures of Scheme 2 not shown in Scheme 1 are discussed in more detail in Examples 9 and 10.

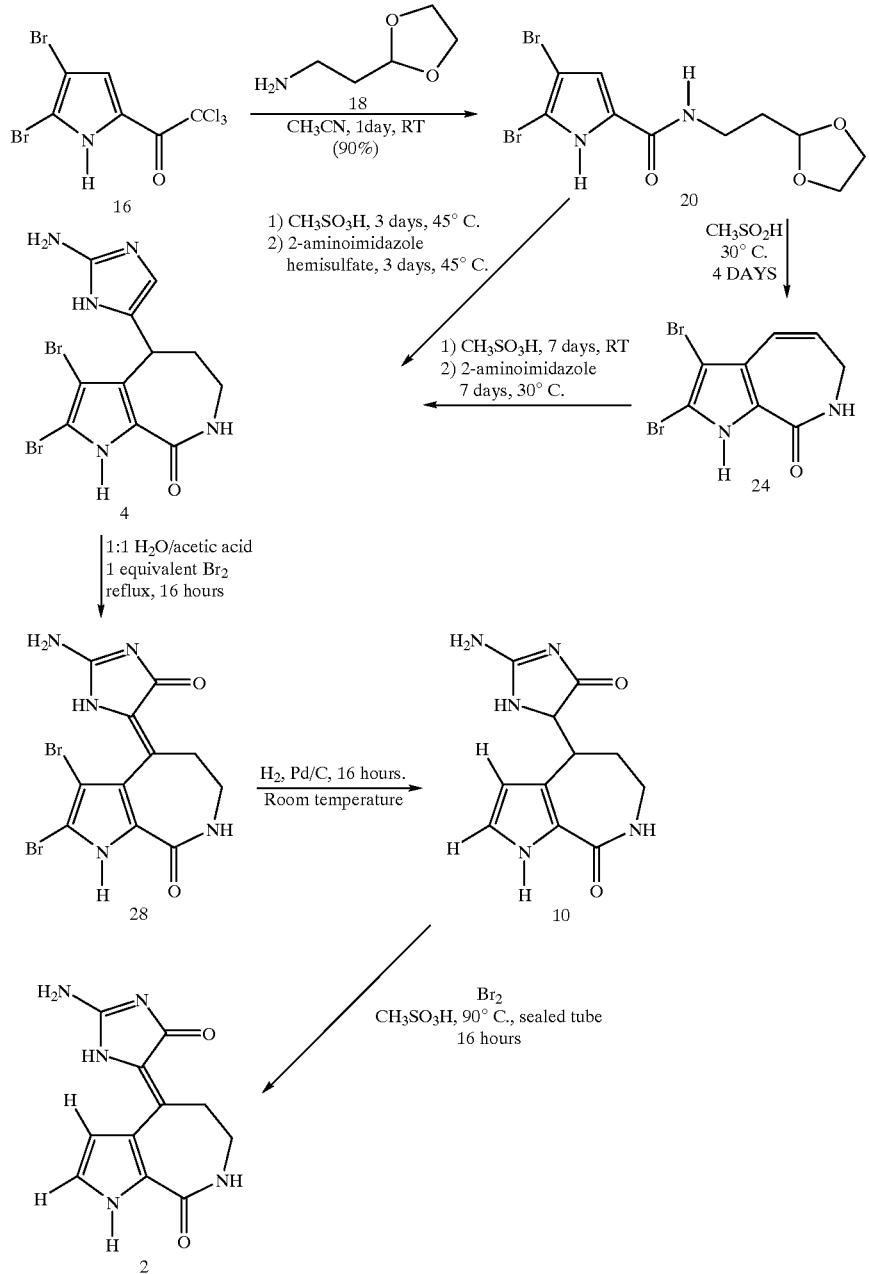

The first step of Scheme 2 is the same as Scheme 1, i.e., the coupling of bromopyrrole 16 with amine 18. The method illustrated by Scheme 2 then proceeds by forming compound 24, and then coupling compound 24 to 2-aminoimidazole to provide hymenin 4. In Scheme 1, the product formed by acetal hydrolysis, i.e., compound 22, was isolated prior to the intramolecular cyclization and reaction with 2-aminoimidazole to form hymenin 4.

In Scheme 1, hymenin 4 first was brominated to form compound 26, followed by the formation of compound 28. Scheme 2 shows that compound 28 can be made directly without isolating compound 26 as with Scheme 1 by reacting hymenin 4 with one equivalent of a halogen, such as bromine, in a solvent system comprising 1:1 water/acetic acid. The remaining steps, i.e., the formation of compound 10 and its conversion to DBH 2, are the same as with Scheme 1.

C. Scheme 3

Scheme 3 below provides another alternative method for forming DBH 2.

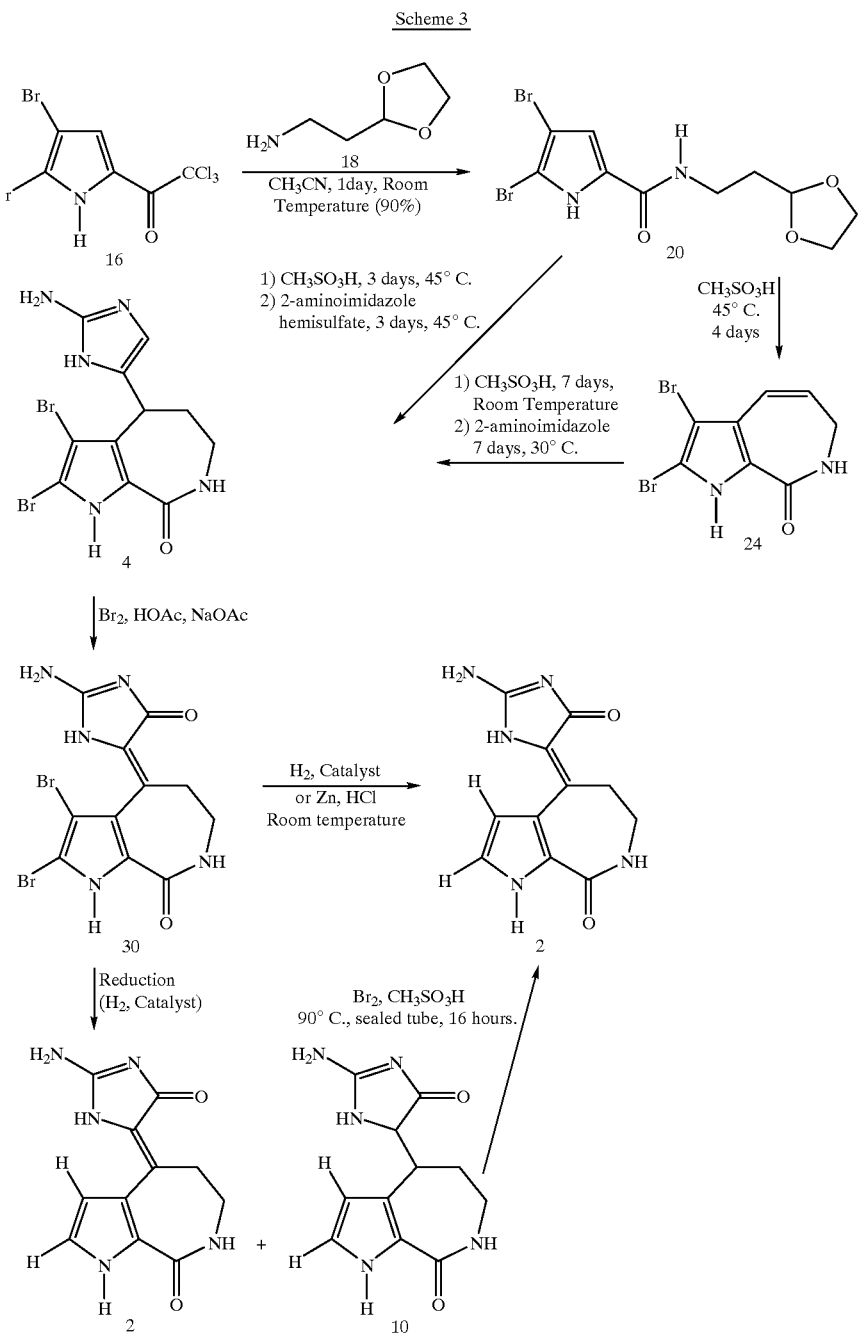

The embodiment of the present method illustrated by Scheme 3 is similar to the embodiments illustrated in Schemes 1 and 2 in that all such methods proceed first by making hymenin 4. But, Scheme 3 shows that hymenin 4 can be oxidized, using any suitable oxidizing reaction conditions, to form a Compound 30. The illustrated oxidation conditions included reacting hymenin 4 with a halogen, such as bromine, in the presence of acetic acid and sodium acetate.

Compound 30 can then be converted to either DBH 2 directly, or can be converted to compound 10, which is itself then converted to DBH 2 as discussed above and illustrated in Schemes 1 and 2. The conversion of compound 30 to DBH 2 requires removing the halogen atoms on the pyrrole ring selectively without simultaneously reducing the olefin between the five- and seven-membered rings. This likely can be accomplished by using a catalyst, such as Lindlar's catalyst. Alternatively, this transformation may be accomplished by reacting compound 30 with other selective reducing agents, such as zinc metal in the presence of a mineral acid, such as hydrochloric acid.

Compound 30 can be converted to compound 10 by removing the halogens from the pyrrole ring, and simultaneously reducing the olefin. One approach to accomplish this is hydrogenation using hydrogen gas and a catalyst, such as palladium on carbon. Once compound 10 is formed, it then can be converted to DBH 2 as described.

Which method illustrated by Scheme 3 is preferred, i.e., forming DBH 2 directly from compound 30, or alternatively first forming compound 10 and then forming DBH 2, depends on several factors, including yields of the reactions, and the purification methods required to purify the desired compounds made by each of the alternative processes.

D. Scheme 4

Scheme 4 illustrates still another embodiment of a method for making DBH 2 and analogs thereof. As with the embodiments illustrated by Schemes 1–3, the method illustrated by Scheme 4 also proceeds by first forming hymenin 4. Hymenin 4 is then converted to DBH 2 though oxidation of Compound 32. Any method for oxidizing Compound 32 to DBH 2 can be used to practice the method. The illustrated conditions included oxidizing Compound 32 using either (1) copper acetate [$Cu(Oac)_2$] and acetic acid/sodium acetate, or (2) sodium hydroxide and water. Scheme 4 provides a method for forming DBH 2 having significantly fewer steps than illustrated for Schemes 1–3.

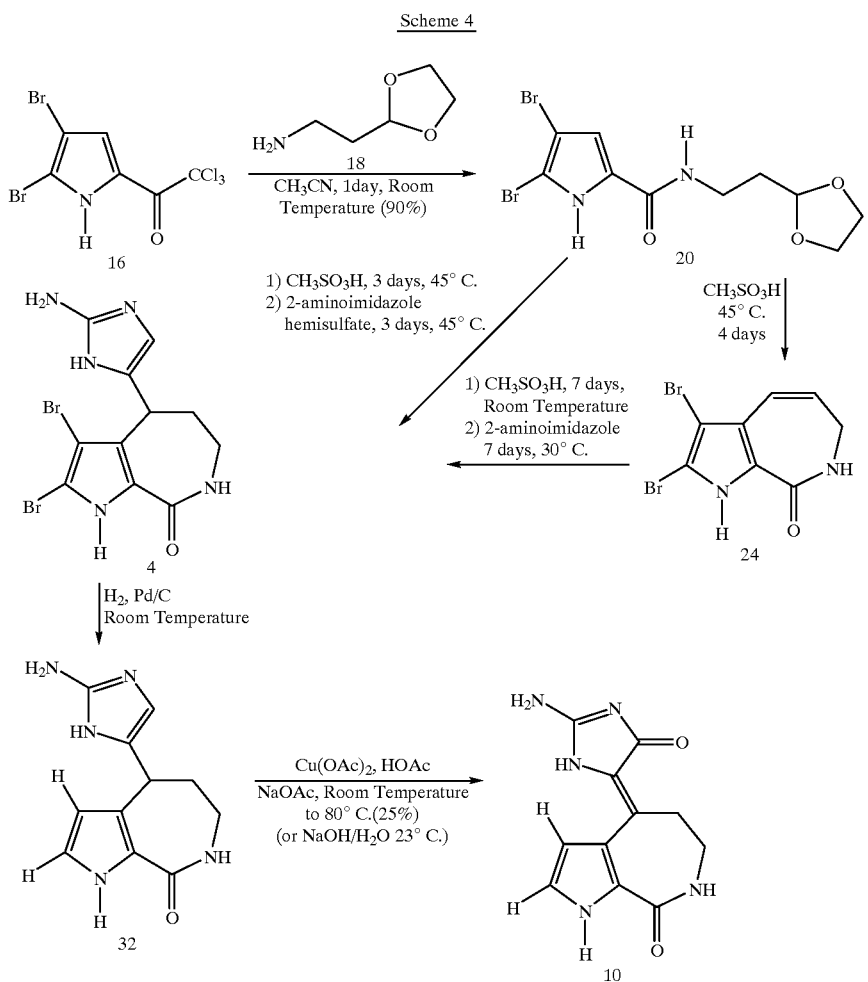

Scheme 4

II. Analogs

The method of the present invention also can be used to make analogs of DBH. These analogs generally have Formula 7.

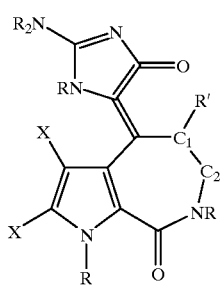

Formula 7

With reference to Formula 7, $C_1$ and $C_2$ are carbon atoms bonded together by a single bond or a double bond; R is independently selected from the group consisting of hydrogen and lower aliphatic, particularly lower alkyl; R' is hydrogen when $C_1$ and $C_2$ are bonded together by a double bond and is selected from the group consisting of hydrogen and lower alkoxy when $C_1$ and $C_2$ are bonded together by a single bond; and X is independently selected from the group consisting of hydrogen and halogen, particularly bromine. For example, alkoxy derivatives, such as Compound 12, can be made according to the method described in Example 8. General structural Formula 4 for such alkoxides is provided below.

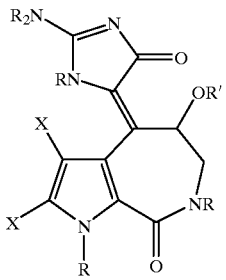

Formula 4

With reference to Formula 4, R is selected from the group consisting of hydrogen and lower aliphatic groups, particularly lower alkyl groups, R' is selected from the group consisting of lower aliphatic groups, particularly lower alkyl; and X is selected from the group consisting of halogen, preferably bromine, and hydrogen. Compounds where R' is other than a methyl group can be made by forming alcoholic mixtures as described in Example 8 using alcohols other than methanol, such as ethanol, propanol, etc.

Products produced by eliminating functional groups, such as the alkoxy group in Formula 4, including the conjugated diene derivatives represented by general Formula 5 below, also can be made using the method of the present invention.

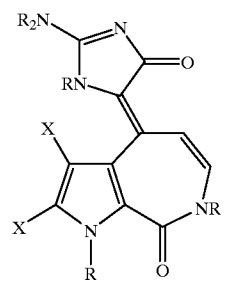

Formula 5

With reference to Formula 5, R is selected from the group consisting of hydrogen and lower aliphatic groups, particularly lower alkyl groups, and X is selected from the group consisting of halogen, preferably bromine, and hydrogen. Compound 14 is one example of a conjugated diene having Formula 5 that can be made by the method of the present invention.

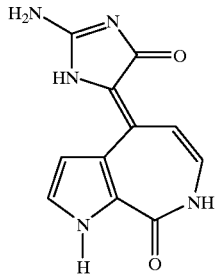

Compound 14

Compound 14 can be made by heating the alkoxy analog to a temperature sufficient to allow for elimination of the alkoxy moiety and provide the diene. Working embodiments have formed compound 14 by heating to about 60° C.

Compounds having Formulas 4 and 5 are not just analogs of DBH, but also can be converted into DBH. This is illustrated below in Scheme 5 with reference particularly to Compounds 12 and 14.

Scheme 5

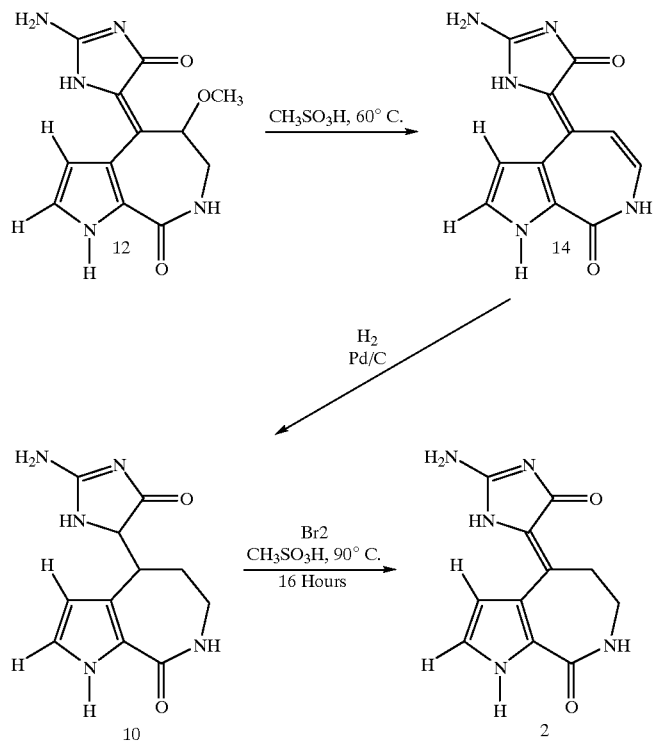

EXAMPLES

The following examples are provided to exemplify certain particular features of working embodiments of the present invention. The scope of the present invention should not be limited to those features exemplified.

Example 1

This example describes the synthesis of acetal 20 of Scheme 1. A 25 milliliter acetonitrile solution of trichloroacetylpyrrole (compound 16, Scheme 1; 11 mmol) [prepared as described in Bailey. D. M., et al., *Journal of Medicinal Chemistry*, 16:1300–1302 (1973)], commercially available aminoacetal 18 (10 mmol) and triethylamine (30 mmol) were stirred at 25° C. for 24 hours under argon. The mixture was partitioned between 150 milliliters of methylene chloride and 100 milliliters of 5% (aqueous) citric acid. The organic layer was washed with saturated NaHCO$_3$ and dried over MgSO$_4$. Concentration afforded a solid, which was recrystallized from acetone/methylene chloride to give compound 20 of Scheme 1 (90% yield) as a colorless solid, melting point=155°–157° C. $^1$HNMR (300 MHz, CD$_3$OD) δ2.73 (td, J=4.7 Hz, 7.1 Hz, 2H), 3.42 (t, J=7.1 Hz, 2H), 3.83 (m, 2H), 3.95 (m, 2H), 4.90 (t, J=4.7 Hz, 1H), 6.76 (s. 1H). IR (Nujol) cm$^{-1}$ 3358, 3110, 1646, 1569, 1530, 1433, 1412, 1372, 1328, 1244, 1136, 905, 837. MS (DCl, CH$_4$) m/z 369 (M$^+$+3, 100), 367 (M$^+$+1.48), 289(13).

Example 2

This example describes the synthesis of aldehyde 22 of Scheme 1. A 70 milliliter acetone/water (1:1) solution of acetal 20 (10 mmol) and p-toluene sulfonic acid monohydrate (5 mmol) was refluxed for 8 hours. The solution was poured into 350 milliliters of methylene chloride, washed with 100 milliliters of saturated NaHCO$_3$, and dried over MgSO$_4$. Concentration afforded a solid, which was recrystallized from ethyl acetate/methylene chloride to give compound 22 (85% yield) as a colorless solid, melting point= 160°–163° C. $^1$H NMR (300 MHz, Acetone-D$_6$) δ2.73 (td, J=6.5 Hz, 1.5 Hz, 2H), 3.63 (q, J=6.5 Hz, 2H), 6.85 (d, J=2.9 Hz, 1 H), 7.63 (br., 1H), 9.75 (t, J=1.5 Hz, 1H), 11.73 (br., 1H). $^{13}$C NMR (300 MHz, Acetone-D$_6$) δ33.9, 44.3, 99.5, 105.6, 113.3, 128.8, 160.3, 201.6.

Example 3

This example describes the synthesis of compound 4 [(±)-hymenin] of Scheme 1 from aldehyde 22. A solution of aldehyde 22 (10 mmol) and 2-aminoimidazole sulfate (12 mmol) in 5 milliliters of methane sulfonic acid was stirred at 25° C. under argon for 5 days. The reaction was neutralized with saturated NaHCO$_3$ and concentrated to afford a solid. The solid was taken up in 75 milliliters of ethanol and filtered. The filtrate was concentrated. Silica gel chromatography of the resulting residue with CH$_2$Cl$_2$/MeOH(NH$_3$), 8:2, afforded a 63% yield of (±)-hymenin 4 as a solid, melting point=86°–90° C. (decomposed). $^1$H NMR (300 MHz, CD$_3$OD), δ1.92 (m, 1H), 2.25 (m, 1H), 3.06 (dd, J=14.0 Hz, 7.3 Hz, 1H), 3.16 (dd, J=14.0 Hz, 9.8 Hz, 1H), 4.12 (t, J=3.5 Hz, 1H), 5.88 (s, 1H). $^{13}$C NMR (300 MHz, CD$_3$OD) δ32.7, 37.9, 38.4, 102.8, 107.7, 113.0, 125.3, 128.5, 136.8, 150.6, 164.2. IR (Nujol) cm$^{-1}$ 3360, 3270, 3150, 1676, 1625, 1566, 1481, 1425, 1327, 1216, 1095, 949. MS(DCl,CH$_4$), m/z390(M$^+$+3.50), 388(M$^+$+1.35), 312(22), 112 (100).

Example 4

(±)-Hymenin 4 also can be produced by first cyclizing aldehyde 22 to form a bromopyrrole intermediate (compound 24 of Scheme 1; brackets around compound 24 indicate that this compound can be, but need not be, isolated and purified). Compound 24 has been converted to (±)-hymenin 4. One embodiment of a method for forming compound 24 proceeded as follows. A solution of aldehyde 22 (10 mmol) in 5 milliliters of methane sulfonic acid was stirred at 25° C. under argon for 3 days. The reaction mixture was neutralized with saturated $NaHCO_3$ and extracted with 200 milliliters of methylene chloride. The organic layer was dried over $MgSO_4$ and concentrated to afford a solid. Silica gel chromatography of the solid with $CH_2Cl_2/MeOH(NH_3)$, 9:1, as the eluent gave compound 24, melting point 172°–175° C. (decomposed), as a colorless solid in 82% yield. $^1H$ NMR (300 MHz, $CD_3OD$) δ3.57 (d, J=6.4 Hz, 2H), 6.01 (dt, J=10.1 Hz, 6.4 Hz, 1H), 6.65 (d, J=10.1 Hz, 1H); $^{13}C$ NMR (300 MHz, $CD_3OD$) δ39.6, 100.2, 108.4, 126.4, 126.7, 126.8, 127.0, 164.6; IR (Nujol) $cm^{-1}$ 3270, 3184, 3020, 1639, 1603, 1541, 1477, 1419, 1265, 1146, 921; MS (DCl, $CH_4$) m/z 307 ($M^+$+3, 100), 305 ($M^+$+1.55), 278 (20), 264 (22).

A solution of pyrrole 24 (10 mmol) and 2-aminoimidazole (12 mmol) in 5 milliliters of methane sulfonic acid was stirred at 25° C. under argon for 5 days. The reaction mixture was neutralized with saturated $NaHCO_3$ and concentrated to afford a solid. The solid was taken up in 75 milliliters of ethanol, filtered, and the filtrate concentrated. Silica gel chromatography of the residue with $CH_2Cl_2/MeOH(NH_3)$, 8:2, provided a 76% yield of (±)-hymenin 4 as a solid, melting point=86°–90° C. (decomposed). $^1H$ NMR (300 MHz, $CD_3OD$): δ1.92 (m,1H), 2.25 (m,1H), 3.06 (dd, J=14.0 Hz, 7.3 Hz, 1H), 3.16 (dd, J=14.0 Hz, 9.8 Hz, 1H), 4.12 (t, J=3.5 Hz, 1H), 5.88 (s. 1H). $^{13}C$ NMR (300 MHz, $CD_3OD$) δ32.7, 37.9, 38.4, 102.8, 107.7, 113.0, 125.3, 128.5, 136.8, 150.6, 164.2. IR (Nujol) $cm^{-1}$ 3360, 3270, 3150, 1676, 1625, 1566, 1481, 1425, 1327, 1216, 1095, 949. MS (DCl, $CH_4$) m/z390($M^+$+3.50), 388($M^+$+1.35), 312 (22), 112 (100).

Example 5

This example describes the synthesis of (±)-4'-bromohymenin (compound 26 Scheme 1). To a stirred solution of (±)-hymenin 4 in 20 milliliters of $CF_3CO_2H$ was added $Br_2$ (0.16 milliliter, 3.1 mmol) at room temperature. After about 20 minutes, the reaction mixture was concentrated under reduced pressure. The resulting residue was purified by flash chromatography ($CH_2Cl_2/MeOH$ saturated with $NH_3$ 9:1) to provide (±)-4'-bromohymenin 26 (1.1 gram, 95%) as a colorless solid. $^1H$ NMR (DMSO-$d_6$): δ1.99 (m, 2H), 3.12 (m, 2H), 4.03 (t, 1H, J=5.2), 5.05(bs, 2H), 7.95(brt, 1H), 10.23 (bs, 1H), 12.50 (br, 1H); IR (Nujol) 3240, 2921, 1617, 1555 $cm^{-1}$; UV ($CH_3OH$) $λ_{max}$277, 213 nm; HRMS, calculated for $C_{11}H_{10}N_5OBr_3(M^+)$ 464.8436, found 464.8427. 26 HCl: $^1H$ NMR ($CD_3OD$): δ2.21–2.13 (m, 2H), 2.33–2.24 (m, 2H), 3.35–3.25 (m 2H), 4.25 (dd, 1H, J=6.8, 5.5); $^{13}C$ NMR ($CD_3OD$): δ34.3(t), 36.5(d), 39.6(t), 96.2(s), 102.4(s), 108.6(s), 124.7(s), 126.1(s), 127.4 (s), 148.9(s), 164.0(s). Anal. Calculated for $C_{11}H_{10}N_5OBr_3$·HCl: C, 26.19; H, 2.20; N, 13.88. Found: C, 26.11; H, 2.30; N, 13.87.

Example 6

This example describes the synthesis of 3-bromo-4,5'-dihydrohymenialdisine 28. A solution of 26 (100 mg, 0.21 mmol) in 10 milliliters of $H_2O$/acetic acid (1:1) was refluxed for 12 hours. The solvent was evaporated under reduced pressure and the resulting residue was purified by flash chromatography ($CH_2Cl_2/MeOH$ saturated with $NH_3$ 8:2) to afford diastereomers, which are referred to herein (but not shown in Scheme 1) as 28a (32 mg, 38%) and 28b (29 mg, 34%) as colorless solids. 28a HCl: $^1H$ NMR (DMSO-$d_6$) δ1.50 (m, 1H), 1.97 (m, 1H), 3.12 (m, 2H), 3.49 (t, 1H, J=8.2), 4.85 (bs, 1H), 7.98 (bt, 1H), 8.88 (bs, 1H), 8.98 (bs, 1H), 9.64 (s, 1H), 12.45 (bs, 1H), 12.67 (s, 1H); $^{13}C$ NMR (DMSO-$d_6$) δ28.0, 37.7, 37.8, 61.4, 99.3, 106.2, 121.9, 125.5, 158.9, 161.8, 173.3; IR (Nujol) 3254, 3127, 1769, 1701, 1622, 1538, 1420, 1195, 1023, 984, 763 $cm^{-1}$; UV ($CH_3OH$) $λ_{max}$ 276, 229 (sh) nm; HRMS, calculated for $C_{11}H_{12}N_5O_2Br_2$ ($MH^+$) 403.9358, found 403.9360. 28b HCl: $^1H$ NMR (DMSO-$d_6$) δ1.80 (m, 1H), 2.08 (m, 1H), 3.10 (m, 2H), 3.52 (q, 1H, J=5.8), 4.59 (d, 1H, J=5.1), 7.89 (bt, 1H), 8.90 (bs, 1H), 9.22 (bs, 1H), 9.88 (s, 1H), 12.36 (bs, 1H), 12.60 (s, 1H); $^{13}C$ NMR (DMSO-$d_6$) δ29.0, 37.5, 37.8, 60.8, 100.0, 105.7, 121.8, 125.5, 157.7, 161.7, 173.1; IR (Nujol) 3264, 1769, 1705, 1626, 1538, 1408 $cm^{-1}$; UV ($CH_3OH$) $λ_{max}$276, 229 (sh) nm; HRMS, calculated for $C_{11}N_{12}N_5O_2Br_2$ ($MH^+$) 403.9358, found 403.9362.

Example 7

This example describes a working embodiment of a method for making compound 10 of Scheme 1. A mixture of compound 28 (0.01 mole), 10% Pd/C, and sodium acetate (0.05 mol) in methanol (50 milliliters) was stirred under a hydrogen atmosphere for 16 hours at room temperature. Filtration of the reaction mixture over Celite, followed by concentration of the solvent, provided compound 10 as a mixture of two diastereomers 10a, 10b (not shown in Scheme 1). Flash chromatography over silica using methylene chloride/methanol (saturated with ammonia, 8:2) allowed separation of the diastereomers into pure components in a combined yield of 85%. Diastereomer 10a, i.e., the diastereomer having the higher $R_f$, $^1H$ NMR (400 MHz, $d_6$-DMSO) δ1.39 (m, 1H), 1.76 (m, 1H), 3.08 (m, 1H), 3.19 (m, 1H), 3.25 (m, 1H), 4.29 (d, 1H, J=2.0), 6.24 (t, 1H, J=2.8), 6.4 (br, 1H), 6.88 (t, 1H, j=2.8), 7.15 (s, 1H), 7.4 (br, 1H), 7.57 (1H, dd, j=6.5, 2.8), 11.15 (bs, 1H). $^{13}C$ NMR (75 MHz, $d_6$-DMSO) δ27.3 (t), 39.3 (t), 39.4 (d), 64.6 (d), 108.7 (d), 121.8 (d), 122.9 (s), 126.1 (s), 163.5 (s), 172.7 (s), 188.1 (s). Diastereomer 10b having the lower $R_f$, $^1H$ NMR (400 MHz, $d_6$-DMSO) δ1.89 (m, 1H), 2.06 (m, 1H), 3.11 (m, 1H), 3.24 (m, 1H), 3.37 (m, 1H), 3.84 (d, 1H, J=1.8), 5.90 (t, 1H, J=2.5), 6.72 (t, 1H, J=2.5), 7.00 (br, 2H), 7.53 (s, 1H), 7.57 (1H, dd, j=5.5, 3.4), 10.99 (bs, 1H). $^{13}C$ NMR (75 MHz, $d_6$-DMSO) δ33.4 (t), 39.5 (t), 39.6 (d), 65.2 (d), 108.7 (d), 121.2 (d), 123.1 (s), 124.1 (s), 163.8 (s), 172.1 (s), 189.1 (s).

Example 8

This example describes a working embodiment for making DBH 2 from Compound 10 of Scheme 1. To a stirred solution of compound 10 (0.01 mole), as a mixture of diastereomers 10a, 10b in methanesulfonic acid (15 milliliters) was added bromine (0.01 mole). The mixture was heated to and maintained at 90° C. in a sealed vessel for 16 hours. The reaction mixture was diluted with ether and decanted three times. The resulting solid was stirred in methanol and neutralized with sodium acetate. Purification by silica gel chromatography (2:8 $CH_2Cl_2$:$CH_3OH$ saturated with ammonia) of the resulting solid provided DBH 2 as a pale yellow solid in about 45% yield. Spectroscopic data for DBH 2 made in this manner was substantially identical to that previously published.

DBHM 12 also was made according to the method described in this Example 8 in about 20% yield.

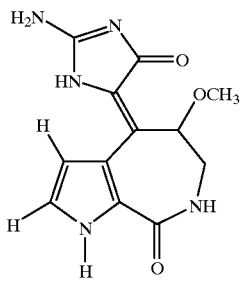

Compound 12

$^1$H NMR (400 MHz, d$_6$-DMSO in the presence of CH$_3$SO$_3$H) δ3.19 (S, 3H), 3.27 (D, 1H, J=14.9), 3.57 (dd, 1H, J=14.9, 6.6), 5.70 (d, 1H, J=6.6), 6.50 (t, 1H, J=2.8), 7.06 (t, 1H, J=2.8), 7.75 (bs, 1H), 8.80 (bs, 1H), 9.45 (bs, 1H), 10.90 (bs, 1H), 11.95 (bs, 1H). $^{13}$C NMR (75 MHz, d$_6$-DMSO) δ42.8 (t), 48.9 (q), 55.9 (q), 68.7 (d), 110.5 (d), 117.0 (s), 122.0 (s), 123.1 (d), 126.8 (s), 129.9 (s), 154.9 (s), 162.2 (s), 163.5 (s).

Example 9

This example concerns the synthesis of compound 4 from compound 20 as illustrated in Schemes 2, 3 and 4 by bypassing compound 22 as illustrated in Scheme 1. A solution of compound 20 (5 mmol) in methanesulfonic acid (10 milliliters) was stirred for 3 days at 45° C. After this time, 2-aminoimidazole hemisulfate (1.6 mmol) was added. The resulting solution was stirred for 7 days. The mixture was then triturated with ether and purification of the resulting material by silica gel chromotography provided pure compound 4 (70%).

Example 10

This example describes the synthesis of compound 28 from compound 4 by bypassing compound 26 as shown in Scheme 2. A solution of compound 4 (5 mmol) in 1:1 mixture of acetic acid:water was treated with bromine (5 mmol) and heated to reflux for 12 hours. Concentration of and silica gel chromotography of the resulting solid provided compound 28 (75% yield) as a mixture of diastereomers.

Example 11

Compound 14 was prepared by heating compound 12 (1 equivalent) in deuterated DMSO (NMR tube experiment) containing approximately 2 equivalents of methanesulfonic acid at 60° C. for 30 hours.

Proton NMR (d$_6$-DMSO): δ6.29 (dd, 1H, J=7.0, 10.8) 6.67 (t, 1H, J=2.5), 7.28 (d, 1H, J=10.8), 7.40 (t, 1H, J=2.9), 8.1–8.9 (br, 2H), 10.17 (d, 1H, J=7.0), 10.8–10.9 (bs, 1H), 12.4–12.5 (bs, 1H), 12.5–12.6 (bs, 1H).

Double pulse field gradient spin echo experiment in which irradiation of beta hydrogen show NOE to imidazolidinone NH thus confirming the stereochemistry of the olefinic double bond as depicted.

Example 12

This example describes the conversion of compound 20 to hymenin 4 as illustrated in Scheme 2. A solution of acetal 20 (1 g) was stirred in methansulfonic acid (3 mL) at 45° C. After 3 days, 2-aminoimdazole hemisulfate (1.2 eq) was added and the mixture was stirred an additional 3 days at 45° C. Trituration with ether and chromatography of the resulting residue afforded racemic hymenin 4 in 65% yield. Spectral data matched those previously reported for racemic hymenin 4.

Example 13

This example describes the conversion of hymenin 4 to 3-bromohymenialdisine 30 as illustrated by Scheme 3. To a solution of hymenin 4, MeSO$_3$H (0.200 g, 0.344 mmol) in HOAc (10 mL), NaOAc (0.141 g, 1.72 mmol), and bromine (0.035 mL, 0.688 mmol) were added. The reaction was stirred for 30 minutes at room temperature. Removal of the solvent in vacuo followed by purification by chromatography (7/3 CH$_2$Cl$_2$, MeOH (NH$_3$)) yielded 3-bromohymenialdisine 30 as a light yellow crystal (70% yield) 1HNMR (DMSO-d$_6$): 3.15 (4H, bs), 6.58 (bs, exch D$_2$O), 7.87 (bs, exch D$_2$O), 7.88 (bs, exch D$_2$O), 8.88 (bs, exch D$_2$O), 13.09 (bs, exch D$_2$O). $^{13}$CNMR (as the HOAc solvate): δ172.8, 165.6, 165.1, 130.4, 127.4, 123.2, 115.9, 108.6, 96.9, 39.7, 34.1. HRMS (FAB) (of pure free base): calcd C$_{11}$H$_9$O$_2$N$_5$Br$_2$ 401. 92025, obsd 401.92012

Example 14

This example describes the conversion of 3-bromohymenialdisine 30 to DBH 2 as shown in Scheme 3. Compound 30 is reduced to form DBH 2 by treatment with hydrogen and Lindlar's catalyst. It currently is believed that it is also possible to accomplish the reduction with Raney nickel, Zn/HOAc, Zn/HCl, ZnAg couple or other zinc reducing reagents.

Example 15

This example describes the conversion of hymenin 4 to didebromohymenin 32 and its subsequent conversion to DBH 2 as illustrated in Scheme 4. Hymenin 4 was converted to didebromohymenin (32) by the method of Xu et. al., J. Org. Chem. p. 456–464, 1997. Didebromohymenin 32 was converted to DBH 2 by treating a solution of didebromohymenin (1 g) in acetic acid (10 mL) with copper (II) acetate (2 eq.). The mixture was stirred in the presence of oxygen between 23° and 60° C. for 16 hours. Concentration and purification by chromatography produced DBH 2. The spectral data matched those previously reported for this compound.

DBH 2 also can be produced by base-catalyzed air oxidation of didebromohymenin 32 by simply stirring didebromohymenin in water in the presence of sodium hydroxide and oxygen at 23° C. This reaction may proceed slowly. It currently is believed that the same conversion can be done with palladium (II) and oxygen by the Wacker process.

The present invention has been described with respect to certain embodiments. The scope of the invention should not be limited to these described embodiments, but rather should be determined by reference to the following claims.

We claim:

1. A method for making debromohymenialdisine and analogs thereof, comprising:

providing hymenin; and converting hymenin into debromohymenialdisine and analogs thereof using a two-step oxidation and reduction process under reaction conditions which provide debromohymenialdisine and analogs thereof.

2. The method according to claim 1 where converting hymenin comprises forming a compound having Formula 1

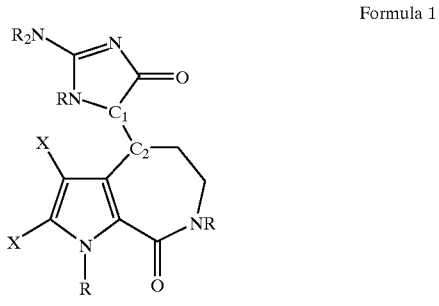

Formula 1 where $C_1$ and $C_2$ are carbon atoms in a single or double bond, R is independently selected from the group consisting of hydrogen and lower alkyl, and X is hydrogen when $C_1$ and $C_2$ are carbon atoms in a single bond and is a halogen when $C_1$ and $C_2$ are carbon atoms in a double bond, or Formula 2

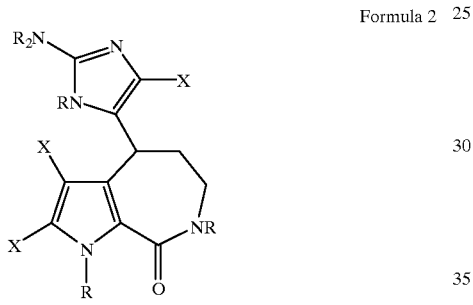

Formula 2 where R is independently selected from the group consisting of hydrogen and lower alkyl, and X is independently selected from the group consisting of hydrogen and halogen other than bromine.

3. The method according to claim 2 where $C_1$ and $C_2$ are carbon atoms in a single bond and converting hymenin to debromohymenialdisine comprises first providing a compound having Formula 3

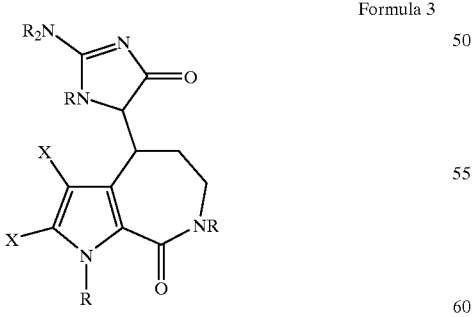

Formula 3 where R is independently selected from the group consisting of hydrogen and lower alkyl, and X is independently selected from the group consisting of hydrogen and halogen when any one of R is lower alkyl and is hydrogen when R is hydrogen.

4. The method according to claim 3 where the compound having Formula 3 is

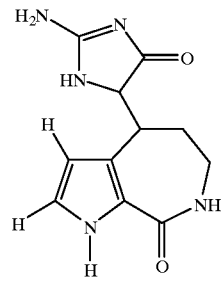

5. The method according to claim 4 where converting the compound having Formula 3 to debromohymenialdisine comprises reacting the compound with a halogen.

6. The method according to claim 5 where the halogen is bromine.

7. The method according to claim 4 where converting the compound having Formula 3 to debromohymenialdisine comprises reacting the compound with a halogen in the presence of an acid.

8. The method according to claim 7 where the halogen is bromine and the acid is methane sulfonic acid.

9. The method according to claim 1 where the analog has Formula 4

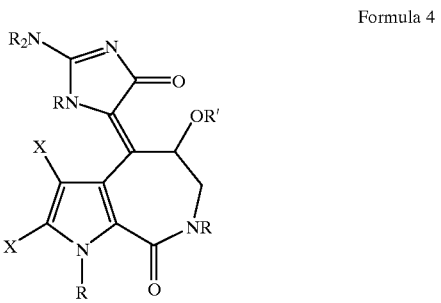

Formula 4 where R is independently selected from the group consisting of hydrogen and lower alkyl, R' is selected from the group consisting of hydrogen and lower alkyl, and X is independently selected from the group consisting of hydrogen and halogen.

10. The method according to claim 9 where all R groups are hydrogen.

11. The method according to claim 9 where all X groups are hydrogen.

12. The method according to claim 9 where all R and X groups are hydrogen.

13. The method according to claim 9 where the analog is

[chemical structure]

14. The method according to claim 1 where the analog has Formula 5

Formula 5

[chemical structure]

where R is independently selected from the group consisting of hydrogen and lower alkyl, and X is independently selected from the group consisting of hydrogen and halogen.

15. The method according to claim 14 where all R groups are hydrogen.

16. The method according to claim 14 where all X groups are hydrogen.

17. The method according to claim 14 where all R and X are hydrogen in Formula 5, and converting comprises first forming the compound having Formula 3 with all R and X hydrogen, and then forming debromohymenialdisine.

18. The method according to claim 3 where providing a compound having Formula 3 first comprises providing a compound having Formula 6

Formula 6

[chemical structure]

where R is hydrogen or lower alkyl, and X is halogen, and the method further comprises converting the compound having Formula 6 to a compound having Formula 3 where R and X are hydrogen.

19. The method according to claim 18 where R of Formula 6 is hydrogen.

20. The method according to claim 18 where the compound having Formula 6 is

[chemical structure]

21. The method according to claim 20 where converting the compound having Formula 6 to a compound having Formula 3 comprises heating the compound in an acidic aqueous solution.

22. The method according to claim 21 where the acidic solution comprises acetic acid.

23. The method according to claim 21 where converting a compound having Formula 6 to a compound having Formula 3 comprises forming

[chemical structure]

and then reacting such compound with hydrogen and a catalyst.

24. The method according to claim 3 where providing a compound having Formula 3 comprises converting hymenin directly to a compound having Formula 3.

25. The method according to claim 24 where hymenin is directly converted to

[chemical structure]

26. The method according to claim 2 where $C_1$ and $C_2$ of Formula 1 are connected by a double bond.

27. The method according to claim 26 where R is hydrogen and X is halogen of Formula 1.

28. The method according to claim 27 where the compound is

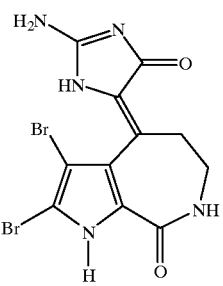

29. The method according to claim 28 where the compound is directly converted to debromohymenialdisine.

30. The method according to claim 29 where the compound is converted to debromohymenialdisine using hydrogen and a catalyst.

31. The method according to claim 30 where the catalyst is selected from the group consisting of metal-based catalysts.

32. The method according to claim 31 where the catalyst is selected from the group consisting of palladium-based catalysts and platinum-based catalysts.

33. The method according to claim 31 where the catalyst is selected from the group consisting of Lindlar's catalyst and Raney nickel.

34. The method according to claim 29 where the compound is converted to debromohymenialdisine using a metal and a mineral acid.

35. The method according to claim 34 where the metal is zinc and the mineral acid is hydrochloric acid.

36. The method according to claim 28 where the compound having Formula 1 is converted to a compound having Formula 3 where R and X are hydrogen.

37. The method according to claim 36 where the compound having Formula 3 is converted to debromohymenialdisine by reacting such compound with a halogen in the presence of an acid.

38. The method according to claim 2 where the compound has Formula 2 with X being hydrogen.

39. The method according to claim 38 where the compound having Formula 2 is oxidized to debromohymenialdisine or an analog thereof.

40. The method according to claim 38 with all R groups being hydrogen.

41. The method according to claim 40 where the compound having Formula 2 is oxidized to debromohymenialdisine.

42. The method according to claim 41 where the compound having Formula 2 is oxidized using copper acetate.

43. The method according to claim 41 where the compound having Formula 2 is oxidized using aqueous sodium hydroxide.

44. The method according to claim 1 where hymenin is formed directly from

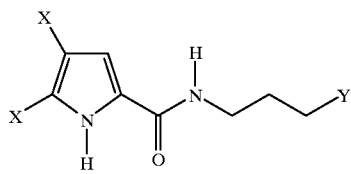

without isolating an intermediate where X is a halogen and Y is a selected from the group consisting of an aldehyde, a functional group capable of conversion to an aldehyde and a protected aldehyde.

45. A method for making debromohymenialdisine, comprising:

providing compound 1

Compound 10

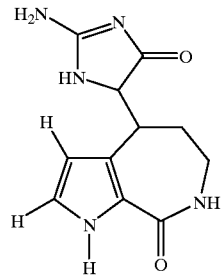

and converting the compound to debromohymenialdisine.

46. The method according to claim 45 where converting Compound 10 comprises reacting the compound with bromine.

47. The method according to claim 46 where bromine is reacted with Compound 10 in the presence of an acid.

48. The method according to claim 47 where the acid is methane sulfonic acid.

49. The method according to claim 45 where providing Compound 10 comprises:

converting hymenin to compound 26

Compound 26

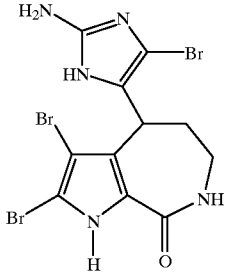

converting Compound 26 to Compound 28

Compound 28

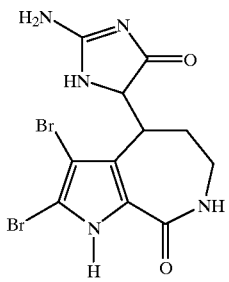

and converting compound 28 to compound 10.

50. The method according to claim 49 where providing Compound 10 comprises:

converting hymenin directly to compound 28; and
converting compound 28 to compound 10.

51. A method for making debromohymenialdisine, comprising:

converting hymenin directly to a compound having a Formula 7

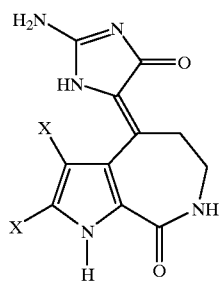

Formula 7 where X is a halogen; and converting the compound having Formula 7 to debromohymenialdisine.

52. The method according to claim 51 where the compound having Formula 7 is directly converted to debromohymenialdisine.

53. The method according to claim 52 where the compound having Formula 7 is directly converted to debromohymenialdisine by reaction with hydrogen and a catalyst.

54. The method according to claim 53 where the catalyst is selected from the group consisting of metal-based catalysts.

55. The method according to claim 53 where the catalyst is selected from the group consisting of palladium-based catalysts and platinum-based catalysts.

56. The method according to claim 53 where the catalyst is selected from the group consisting of Pd/C, Lindlar's catalyst and Raney nickel.

57. The method according to claim 52 where the compound having Formula 7 is directly converted to debromohymenialdisine by reaction with a metal and a mineral acid.

58. The method according to claim 57 where the metal is zinc.

59. The method according to claim 51 where the compound having Formula 7 is first converted to Compound 1

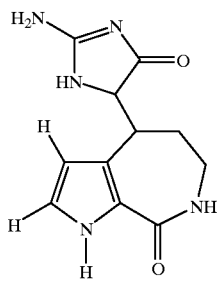

Compound 10

60. The method according to claim 59 where Compound 10 is converted to debromohymenialdisine by reacting the compound with bromine.

61. The method according to claim 56 where Compound 10 is reacted with bromine in the presence of an acid.

62. The method according to claim 61 where the acid is methane sulfonic acid.

63. A method for making debromohymenialdisine, comprising:

converting hymenin directly to Compound 32

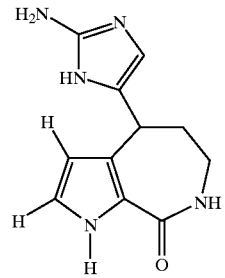

Compound 32 and converting Compound 32 to debromohymenialdisine.

64. The method according to claim 63 where Compound 32 is directly converted to debromohymenialdisine.

65. The method according to claim 64 where Compound 32 is directly converted to debromohymenialdisine by reacting such compound with copper acetate.

66. The method according to claim 64 where Compound 32 is directly converted to debromohymenialdisine by reacting such compound with aqueous sodium hydroxide.

67. A compound having Formula 8

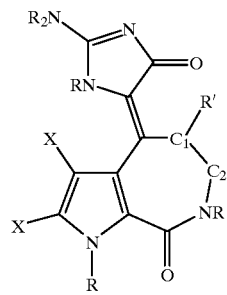

Formula 8 where $C_1$ and $C_2$ are carbon atoms bonded together by a single bond or a double bond, R is independently selected from the group consisting of hydrogen and lower alkyl, R' is hydrogen when $C_1$ and $C_2$ are bonded together by a double bond and is lower alkoxy when $C_1$ and $C_2$ are bonded together by a single bond and X is independently selected from the group consisting of hydrogen and halogen.

68. The compound according to claim 67 where $C_1$ and $C_2$ are bonded together by a single bond.

69. The compound according to claim 68 where all R groups are hydrogen.

70. The compound according to claim 68 where all X groups are hydrogen.

71. The compound according to claim 67 where all R groups are hydrogen and R' is lower alkoxy.

72. The compound according to claim 71 where all X groups are halogen.

73. The compound according to claim 67 having the formula

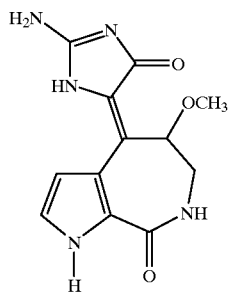

74. The compound according to claim 67 where $C_1$ and $C_2$ are bonded together by a double bond.

75. The compound according to claim 74 where all R groups are hydrogen.

76. The compound according to claim 74 where all X groups are hydrogen.

77. The method according to claim 63 where Compound 32 is directly converted to debromohymenialdisine by reaction with palladium (II) and oxygen.

78. The method according to claim 30 where the compound is converted to debromohymenialdisine using hydrogren and palladium/carbon.

* * * * *

UNITED STATES PATENT AND TRADEMARK OFFICE
CERTIFICATE OF CORRECTION

PATENT NO. : 6,211,361 B1
DATED : April 3, 2001
INVENTOR(S) : Horne et al.

It is certified that error appears in the above-identified patent and that said Letters Patent is hereby corrected as shown below:

Column 2,
Line 21, "42;" should be -- 42: --.
Line 25, "osteooarthritis" should be -- osteoarthritis --.

Column 6,
Line 18, "can comprises" should be -- can comprise --.

Column 7,
Line 11, "is a selected" should be -- is selected --.

Column 11,
Line 17, "Rt" should be -- RT --.
Line 37, "CH$_2$" should be -- CH$_3$ --.

Signed and Sealed this

Seventh Day of May, 2002

Attest:

*Attesting Officer*

JAMES E. ROGAN
*Director of the United States Patent and Trademark Office*